United States Patent [19]

Jaynes et al.

[11] Patent Number: 5,000,034
[45] Date of Patent: Mar. 19, 1991

[54] SHORT-TERM ENGINE OIL SLUDGE TEST

[75] Inventors: Scot E. Jaynes, Eastlake; Kirk E. Davis, Euclid, both of Ohio

[73] Assignee: The Lubrizol Corporation, Wickliffe, Ohio

[21] Appl. No.: 524,270

[22] Filed: May 15, 1990

[51] Int. Cl.$^5$ ............................................ G01M 15/00
[52] U.S. Cl. ............................................ 73/64; 73/116
[58] Field of Search ................ 73/64, 116, 64.1, 61.2, 73/61.3

[56] References Cited

U.S. PATENT DOCUMENTS

| | | | |
|---|---|---|---|
| 2,450,603 | 10/1948 | Lomasney | 73/64 |
| 2,669,865 | 2/1954 | Cole et al. | 73/64 |

OTHER PUBLICATIONS

Procedures of The Engine Oil Review Committee of Engine Oils Under Military Specifications MIL-L-2104D, MIL-L-21260C, MIL-L-46152C and MIL-L-46167A, Appendix B, Society of Automotive Engineers, Nov. 1987.
C. C. Colyer et al., Society of Automotive Engineers Paper No. 885018 (entire document).

*Primary Examiner*—Jerry W. Myracle
*Attorney, Agent, or Firm*—Joseph P. Fischer; Frederick D. Hunter; James L. Cordek

[57] ABSTRACT

A short-term test procedure for comparing the engine sludge performance of different engine oils to a reference oil. The test procedure involves establishing a base line by operating one or more engines on the reference oil while maintaining a substantially constant volume of the reference oil in the engines without changing the oil until a Coordinating Research Council (CRC) sludge rating within a preferred range of 8.5 to 9.0 is achieved. In like manner, a series of engine tests are performed on one or more test oils using engines substantially identical to the reference oil engines for substantially the same number of miles as the average test miles of all of the reference oil engines under substantially the same test conditions as the reference oil engines while maintaining substantially the same volume of the test oil in the engines as the reference oil without changing the test oil in the engines throughout the tests. The average overall sludge rating for each test oil is then calculated based on all of the tests on each test oil, and compared to the average overall sludge rating for the reference oil to determine relative sludge performance.

41 Claims, 1 Drawing Sheet

SHORT-TERM ENGINE OIL SLUDGE TEST

FIELD OF THE INVENTION

This invention relates to a short-term test procedure or method for comparing the relative sludge performance of different formulated engine oils or lubricants in spark ignited internal combustion engines as well as in certain types of diesel engines. As used herein, the term engine oil(s) refers to a formulated engine oil which acts as a lubricant.

BACKGROUND OF THE INVENTION

Sludge formation in spark ignited internal combustion engines as well as in certain types of diesel engines (hereinafter engines) is caused by a number of factors including engine design, engine operating conditions, fuel and oil.

To determine the effects of different engine oils on sludge formation, both engine sequence testing in the lab, such as the Ford VE test, and field testing are used.

Field testing is a significantly less controllable test environment than the engine laboratory. However, with appropriate test design and coordination, all key test parameters can be reasonably controlled.

Heretofore, the usual test for determining the effects of different engine oils on sludge formation in engines involved determining the sludge ratings for the different oils after running the oils in substantially identical engines for 60,000 miles or more under controlled operating conditions that included changing the oil and filter in each engine at predetermined intervals. The major drawback to these standard field tests is that they take a relatively long period of time to complete. Also, most engine lubricant formulations used today are of SG/CC or better quality, which will not normally produce any significant sludge accumulations in engines during these standard long-term field tests.

SUMMARY OF THE INVENTION

The present invention relates to a test procedure or method of comparing different engine oils by sludge performance in substantially less time than the standard long-term tests currently employed. This new short-term test procedure involves establishing a base line by testing one or more reference or base engine oils having known field performance in spark ignited and/or diesel engines. A substantially constant volume of the reference oil is maintained in one or more engines, without changing the reference oil throughout the tests to accelerate sludge formation. The reference oil engines are taken off test when a Coordinating Research Council (CRC) rating for sludge deposits falls within a predetermined range.

The CRC sludge rating for the reference oil is desirably within a range of approximately 7.0 to 9.0 when the test is stopped, with a range of approximately 8.5 to 9.0 being preferred. Also, the severity of the test conditions is desirably controlled so that the engine(s) with the reference oil is required to be driven between approximately 5,000 miles and 25,000 miles before the sludge rating is in such predetermined range, with 12,000 miles to 16,000 miles being preferred.

Further in accordance with this new short-term test procedure, one or more test oils are also tested in engines that are substantially identical to those used for the reference oils. The test oil engines are driven for substantially the same number of miles under substantially the same test conditions as the reference oil engines, while maintaining substantially the same volume of test oil as the reference oil without changing the test oil throughout the tests. After the test oil engines have been driven substantially the same number of miles as the reference oil engines, the test oil engines are taken off test and the sludge rating of the engines on the test oil is determined and compared to the sludge rating of the engines on the reference oil to determine the relative sludge performance of the test oil.

This short-term sludge test procedure is primarily intended to be performed in the field rather than the laboratory, in that laboratory tests do not always adequately predict the performance of engine oils in the field. However, virtually the same tests performed in a static test engine in the lab for substantially the same length of time on the test oils as on the reference oil could have some merit in comparing the sludge performance of different test oils to a reference oil with known field performance. Accordingly, unless indicated otherwise, whenever used in the claims, the term "duration" is intended to cover either field tests in which the engines are operated substantially the same number of test miles or lab tests in which static test engines are operated for substantially the same length of time.

To the accomplishment of the foregoing and related ends, the invention, then, comprises the features hereinafter fully described and particularly pointed out in the claims, the following description and the annexed drawings setting forth in detail certain illustrative embodiments of the invention, these being indicative, however, of but several of the various ways in which the principles of the invention may be employed.

DETAILED DESCRIPTION OF THE PREFERRED EMBODIMENTS

Figure 1:
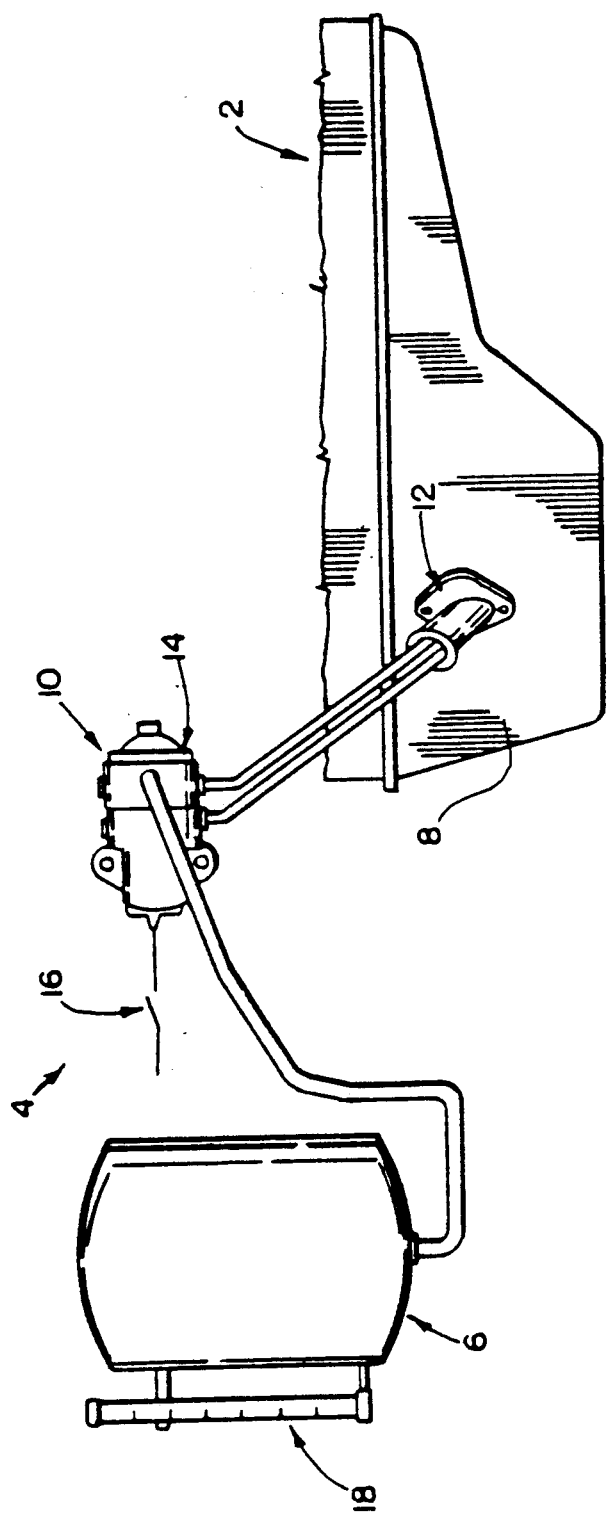
FIG. 1 is a schematic illustration of a test engine for use in testing engine oils for sludge performance according to this invention which includes an oil level control system for maintaining a substantially constant volume of oil in the engine throughout the test procedure.

The short-term test procedure of the present invention is designed to show the relative capabilities of different engine oils in protecting spark ignited and/or diesel engines against sludge. Briefly, this is accomplished by comparing the amount of sludge formed in one or more engines run on a reference or base oil in accordance with certain test parameters described hereafter to the amount of sludge formed in substantially identical engines run on the test oils using substantially the same test parameters for substantially the same number of test miles as the reference oil.

The engines used in the tests must be substantially identical, that is, the same model engines must be used, preferably sequentially produced engines from the same assembly line. The engines may be disassembled, measured and rebuilt, or used as is from the factory as desired. Also, the engines should be randomly distributed for use with all of the oils on test. If the engines have never been used, the engines should be operated, for example, approximately 2,000 miles to break them in, and the oil changed prior to the tests.

All of the engines used in the tests are operated at substantially the same volume of oil for substantially the same number of miles. The actual volume of oil used in the engines may be increased or decreased prior to commencement of the tests depending on such factors as the type of engines used, the severity of the test conditions including traffic, terrain, and climatic or weather conditions, the type of engine oil being tested, and the desired range of sludge rating to be achieved in the reference oil.

If the test conditions are relatively severe, a greater volume of oil is desirably used than if the test conditions are less severe. Using less oil in the engines puts greater stress on the oil thereby reducing the number of miles the engines have to be driven in order to obtain the desired range of sludge rating in the engines on the reference oil. This is particularly important when the driving conditions are less severe.

To establish a base line for the test oils, one or more engines with the reference oil are first driven until the engines reach a standard CRC sludge rating within a predetermined range, for example, 7.0 to 9.0, with a range of approximately 8.5 to 9.0 being preferred.

The objective in running the base line tests is to obtain enough sludge in the base or reference oil engines to be able to make a valid comparison of the sludge performance of the test oils to that of the reference oil using substantially the same test parameters. If the selected CRC base line sludge rating for the engines on the reference oil was greater than about 9.0, there would be very little room for improvement in the test oils, making it very difficult to determine if the test oils perform better than the reference oil. By the same token, if the CRC base line sludge rating for the engines on the reference oil was selected to be below about 7.0, it could also make it difficult to determine if the test oils perform worse than the reference oil. Also, selecting a CRC base line sludge rating below 7.0 could greatly increase the time to complete the tests.

The number of miles that the base line engines with the reference oil must be operated to achieve a sludge rating within the desired range will vary depending on the severity of test conditions, type of engine, and the type and volume of oil used. Whenever possible these parameters are desirably controlled so that the sludge rating within the desired range is achieved when the baseline engines have been driven a minimum of approximately 5,000 miles and a maximum of approximately 25,000 miles, with a range of approximately 12,000 to 16,000 miles being preferred. If more than one engine is used to establish the base line, the less miles the base line engines are driven to produce the desired sludge, the greater the impact any variations in the number of miles each base line engine is driven will have on the validity of the test results. Conversely, if the base line engines are driven too many miles to obtain the desired sludge, the longer it will take to complete the tests. A primary objective of this short-term sludge test procedure is to compare the relative sludge performance of different engine oils in substantially less time than the usual long term field tests, for example, in approximately one-sixth the time or less.

During these short-term sludge tests, it is important that the oil volume in the engines be maintained substantially constant and that the oil not be changed throughout the tests. Satisfactory results should be obtained as long as the level of oil in the engines is maintained within approximately one-half liter or less of the desired level. One way of accomplishing this in accordance with the present invention is by providing each engine (2) with an oil level control system (4) which, as schematically shown in FIG. 1, comprises an oil reservoir (6) connected to the engine crankcase (8) by means of an oil pump (10). The oil reservoir (6) contains a reserve supply of a reference or test oil for the respective engines. The volume of oil in the engine (2) is detected by a probe adaptor (12) suitably connected to the engine crankcase (8) and associated oil level detector (14). A series of switches (16) in parallel with the oil level detector (14) allow oil to be pumped to the engine (2) when the engine is at idle and in level condition and the oil volume in the engine is less than the probe set point.

Engine oil consumption may be monitored during the tests as by providing the oil reservoir (6) with a sight glass (18) marked, for example, in one liter increments. At the beginning of each test, a known quantity of oil, for example, 4 liters, is added to the oil reservoir. Also, a known quantity of oil is added to the engine through the oil fill cap. During the test, additional oil is added to the oil reservoir, for example, in one liter increments, as needed. At the end of each test, the oil is completely drained from the engine and weighed. The difference between the initial and final oil weights are then added to the total weight of incremental amounts of oil added to the reservoir throughout the test as well as the difference between the amount of oil in the reservoir at the beginning and at the end of the test to determine the oil consumption of the engine during the test.

The principal reason for monitoring the oil consumption during each test is to determine what effect, if any, oil consumption has on the validity of the test results. If the test results are inconsistent, and large variations in oil consumption are seen, those test results may have to be invalidated.

To expedite testing, engines using the test oils can be commenced before the base line tests are completed. However, the base line tests on the reference oil must be completed sufficiently in advance of the completion of the tests on the test oils in order to establish the base line for the test oils including particularly the number of miles that the test oil engines are to be driven. This is determined during the base line tests by periodically stopping the base line engines and removing the rocker covers to visually inspect the amount of sludge on the rocker covers. When the desired sludge rating within the predetermined range, for example, 8.5 to 9.0, is achieved on the rocker covers, the base line engines are taken off test, the average test miles calculated, and the average sludge rating determined.

A statistically significant number of engine tests, for example three or more, should preferably be run on all of the oils being tested, including the reference oil, and the results averaged as described hereafter.

If more than one engine test is run on the reference oil to establish the base line for the test oils, each of the base line engines is taken off test when the desired sludge rating on the respective rocker covers, within the predetermined range, is achieved, following which an average overall sludge rating and average test miles for the reference oil based on all such tests is calculated.

The engines for the test oils are substantially identical to the engines for the reference oil and are run for substantially the average number of test miles for all of the engines on the reference oil, while maintaining substantially the same volume of test oil in the respective engines as the reference oil without changing the test oil throughout the respective tests. Also, the test oil engines should be operated under substantially the same test conditions, including the same type of traffic, climatic conditions and terrain. After the test oil engines have been driven substantially the average number of test miles as all of the reference oil engines, the sludge rating for each test oil engine is determined and an average overall sludge rating for each test oil based on all of the tests for each test oil is calculated and compared to that of the reference oil to determine the relative sludge performance of each test oil to the reference oil.

As previously indicated, laboratory tests do not always adequately predict the performance of engine oils in the field. Accordingly, this short-term sludge test procedure is primarily intended to be run in the field. However, it is to be understood that virtually the same tests performed in a static test engine in the lab for substantially the same length of time on the test oils as on the reference oil could have some merit in comparing the sludge performance of different test oils to a reference oil with known field performance. Accordingly, unless indicated otherwise, whenever used in the claims, the term "duration" is intended to cover either field tests or lab tests in which the test engines are either operated for substantially the same number of miles or substantially the same length of time, respectively.

From the foregoing, it will now be apparent that the short-term sludge test procedure of the present invention provides a relatively simple and yet effective way of comparing the sludge performance of different engine oils in substantially less time than required to perform the standard long-term tests now in use.

Although the invention has been shown and described with respect to certain preferred embodiments, it is obvious that equivalent alterations and modifications will occur to others skilled in the art upon the reading and understanding of the specification. The present invention includes all such equivalent alterations and modifications, and is limited only by the scope of the claims.

We claim:

1. A method of comparing sludge performance of different engine oils comprising the steps of:
   (a) establishing a base line by testing a reference oil in an internal combustion engine while maintaining a substantially constant volume of the reference oil in the engine without changing the oil throughout the test, and stopping the test when a sludge rating within a predetermined range for the engine is achieved,
   (b) evaluating a test oil in a substantially identical engine by operating the engine on the test oil for substantially the same duration under substantially the same test conditions as the engine on the reference oil while maintaining substantially the same volume of test oil as the reference oil without changing the test oil throughout the test,
   (c) determining the sludge rating for the test oil based on such test, and
   (d) comparing the sludge rating of the test oil to the sludge rating of the reference oil.

2. The method of claim 1 wherein the testing of the reference oil is completed before completing the testing of the test oil.

3. The method of claim 1 which is performed in the field, and test parameters are selected that require the reference oil to be field tested between approximately 5,000 and 25,000 miles before the sludge rating for the engine on the reference oil is achieved.

4. The method of claim 1 which is performed in the field, and test parameters are selected that require the reference oil to be field tested between approximately 12,000 and 16,000 miles before the sludge rating for the engine on the reference oil is achieved.

5. The method of claim 1 wherein the predetermined range of sludge rating for the engine on the reference oil is selected to be between about 7.0 and 9.0 according to the CRC rating system.

6. The method of claim 1, wherein the predetermined range of sludge rating for the engine on the reference oil is selected to be between about 8.5 and 9.0 according to the CRC rating system.

7. The method of claim 1 wherein the reference and test oils in the respective engines are automatically maintained at substantially the same level throughout the respective tests.

8. The method of claim 1 wherein each of the engines is provided with an oil level control system for automatically maintaining a substantially constant oil level in each engine throughout the respective tests.

9. The method of claim 1 further comprising the step of monitoring the oil consumption of each engine throughout the respective tests.

10. The method of claim 1 which is performed in the field, by running a minimum of three field tests engines on the reference oil using substantially identical engines, the test oil is field tested for substantially the average test miles for all of the engines on the reference oil, and the average overall sludge rating for the reference oil and overall sludge rating for the test oil are calculated and compared to determine the relative sludge performance of the test oil to the reference oil.

11. The method of claim 10 wherein a minimum of three field tests engines are run on the test oil using substantially identical engines for substantially the average test miles for all of the engines on the reference oil, and the average overall sludge rating for the test oil is calculated and compared to the average overall sludge rating for the reference oil to determine the relative sludge performance of the test oil.

12. The method of claim 11 wherein additional test oils are evaluated under substantially the same test conditions and the average overall sludge ratings for the additional test oils calculated and compared to the average overall sludge ratings for the reference oil and other test oils for determining relative sludge performance.

13. The method of claim 1, wherein the engines are broken in and the oil is changed prior to commencing the respective tests.

14. The method of claim 1 wherein the test conditions are relatively severe and the volume of oil in all of the engines is maintained substantially full throughout the respective tests.

15. The method of claim 1 wherein the test conditions are relatively moderate and the volume of oil in all of the engines is maintained at a level substantially less than full throughout the respective tests to increase the stress on the oil during such tests.

16. The method of claim 15 wherein the volume of oil in all of the engines is maintained approximately one liter below full throughout the respective tests to increase the stress on the oil during such tests.

17. The method of claim 1 wherein the volume of oil that is maintained in the engines throughout the respective tests is selected according to the severity of the test conditions, with the volume of oil being greater under more severe test conditions and less under less severe test conditions.

18. The method of claim 1 wherein each of the engines is provided with an oil level control system which automatically delivers additional oil to the respective engines when the engines are operating at idle and are level, and the oil level drops below a predetermined set point to maintain the oil at the desired level throughout the respective tests.

19. The method of claim 18 further comprising the step of calculating the oil consumption of each engine during the respective tests.

20. The method of claim 18 wherein the oil level control system includes an oil reservoir connected to each engine containing an additional supply of reference or test oil for the respective engines, said oil reservoir having a sight glass marked in increments to measure the amount of oil in the reservoir, further comprising the step of adding additional incremental amounts of oil to the reservoir as needed during the respective tests.

21. The method of claim 18 wherein a known quantity of oil is added to each engine at the beginning of the respective tests, further comprising the step of draining the oil from the engines and weighing the oil at the end of the respective tests, calculating the difference between the initial and final oil weights in the engine, and adding such difference to the total weight of oil added to the respective engines throughout the respective tests to calculate the oil consumption for the respective engines during the tests.

22. The method of claim 21, wherein the oil level control system includes an oil reservoir for each engine containing an additional supply of reference or test oil for the respective engines, said oil reservoir having a sight glass marked in increments to measure the amount of oil in the reservoir, the additional oil added to the respective engines during the tests being determined by providing a known quantity of oil in each reservoir at the beginning of the respective tests, adding additional incremental amounts of oil to each reservoir as needed during the respective tests, calculating the incremental amounts of oil added to each reservoir throughout the respective tests, and adding to that the difference between the amount of oil in each reservoir at the beginning and at the end of the respective tests as determined by sight glass readings.

23. The method of claim 1, wherein all of the tests are performed in the field under substantially the same test conditions including particularly substantially the same traffic and climatic conditions.

24. The method of claim 1 wherein all of the tests on the reference and test oils are performed in a static test engine in a lab for substantially the same length of time under substantially the same test conditions.

25. A method of comparing the engine sludge performance of one or more test oils to a reference oil in the field comprising the steps of:
(a) establishing a base line by running a minimum of three field tests engines on a reference oil using substantially identical engines while maintaining substantially the same volume of reference oil in the respective engines without changing the reference oil throughout the tests, stopping each test when a sludge rating within a predetermined range is achieved for each engine, and calculating an average overall sludge rating for the reference oil based on all such tests,
(b) running a minimum of three field tests engines on one or more test oils using substantially identical engines for substantially the average test miles for all of the engines on the reference oil while maintaining substantially the same volume of test oil in the respective engines as the reference oil without changing the test oil throughout the respective tests,
(c) calculating an average overall sludge rating for each test oil based on all such tests of each test oil, and
(d) comparing the average overall sludge rating for each test oil to that of the reference oil.

26. The method of claim 25 wherein the field testing of the reference oil is completed before completing the field testing of the test oil.

27. The method of claim 25 wherein each engine is provided with an oil level control system for automatically maintaining a substantially constant oil level in each engine throughout the respective tests.

28. The method of claim 25 wherein test parameters are selected to require the engines on the reference oil to be field tested between approximately 5,000 and 25,000 miles before the sludge rating for the engines on the reference oil is achieved.

29. The method of claim 25 wherein test parameters are selected for the tests that require the reference oil to be field tested between approximately 12,000 and 16,000 miles before the sludge rating for the engines on the reference oil is achieved;

30. The method of claim 25 wherein the predetermined range of sludge rating for the engines on the reference oil is selected to be between about 7.0 and 9.0 according to the CRC rating system.

31. The method of claim 25 wherein the predetermined range of sludge rating for the engines on the reference oil is selected to be between about 8.5 and 9.0 according to the CRC rating system.

32. The method of claim 25 further comprising the step of calculating the oil consumption of each engine during the respective tests.

33. The method of claim 25 further comprising the step of operating the engines to break the engines in and changing the oil before commencing the respective field tests.

34. The method of claim 25 wherein the level at which the oil is maintained within the engines throughout the tests is selected according to the severity of the test conditions, the level being greater when the test conditions are relatively severe and less when the test conditions are less severe.

35. A short-term field test for comparing the engine sludge performance of one or more test oils to a reference oil comprising the steps of:
(a) establishing a base line by running a series of field tests engines on a reference oil using substantially identical engines under substantially the same test conditions while maintaining a substantially constant volume of the reference oil in the engines without changing the oil in the engines throughout the respective tests, taking the engines on the reference oil off test when a sludge rating within a predetermined range for the engines is achieved, and calculating an average overall sludge rating for the reference oil based on all such tests,
(b) running a series of field tests engines on one or more test oils using engines substantially identical to the engines on the reference oil for substantially the same number of miles as the average test miles of all of the engines on the reference oil under substantially the same test conditions as the reference oil while maintaining substantially the same volume of the test oil in the engines as the reference oil without changing the test oil in the engines throughout the respective tests, (c) calculating an average overall sludge rating for each test oil based on all such tests on each test oil, and (d) comparing the average overall sludge rating for each test oil to the average overall sludge rating for the reference oil to determine relative sludge performance.

36. The method of claim 35 wherein an average overall sludge rating for each engine is calculated prior to calculating the average overall sludge rating for each oil.

37. The method of claim 35 wherein the engines on the reference oil are periodically checked for sludge during the field tests to determine when the sludge rating within the predetermined range for the engines on the reference oil is achieved.

38. The method of claim 35 wherein the rocker covers for the engines on the reference oil are periodically checked for sludge during the field tests to determine when the sludge rating within the predetermined range for the engines on the reference oil is achieved.

39. A short-term field test for comparing the engine sludge performance of one or more test oils to a reference oil comprising the steps of:

(a) establishing a base line by running a series of field tests engines on a reference oil using substantially identical engines under substantially the same test conditions while maintaining a substantially constant volume of the reference oil in the engines without changing the oil in the engines throughout the respective tests, taking each of the engines on the reference oil off test when a CRC sludge rating for each of the engines of between 8.5 and 9 is achieved, and calculating an average overall sludge rating for the reference oil based on all such tests, (b) running a series of field tests engines on each test oil using engines substantially identical to the engines on the reference oil for substantially the same number of miles as the average test miles of all of the engines on the reference oil under substantially the same traffic and climatic conditions while maintaining substantially the same volume of the test oil in the engines as the reference oil without changing the test oil in the engines throughout the respective tests, (c) calculating an average overall sludge rating for each test oil based on all such tests on each test oil, and (d) comparing the average overall sludge rating for each test oil to the average overall sludge rating for the reference oil for determining relative sludge performance.

40. The method of claim 39 wherein all of the engines used in the tests are substantially identical spark ignited engines.

41. The method of claim 39 wherein all of the engines used in the tests are substantially identical diesel engines.

* * * * *